(12) United States Patent
McDermott et al.

(10) Patent No.: US 10,890,544 B1
(45) Date of Patent: Jan. 12, 2021

(54) NUCLEAR DENSITOMETER ASSEMBLIES FOR HYDRAULIC FRACTURING

(71) Applicant: Field Service Solutions LLC, League City, TX (US)

(72) Inventors: Justin McDermott, League City, TX (US); Joshua Littlejohn, League City, TX (US); Floyd Allen Kennedy, League City, TX (US)

(73) Assignee: Field Service Solutions LLC, League City, TX (US)

( * ) Notice: Subject to any disclaimer, the term of this patent is extended or adjusted under 35 U.S.C. 154(b) by 0 days.

(21) Appl. No.: 16/719,754

(22) Filed: Dec. 18, 2019

(51) Int. Cl.
| | | |
|---|---|---|
| *G01N 23/06* | (2018.01) | |
| *G01N 23/083* | (2018.01) | |
| *G01N 23/087* | (2018.01) | |
| *G01N 23/12* | (2018.01) | |
| *G01N 33/28* | (2006.01) | |

(52) U.S. Cl.
CPC ............ *G01N 23/12* (2013.01); *G01N 23/06* (2013.01); *G01N 23/083* (2013.01); *G01N 23/087* (2013.01); *G01N 33/28* (2013.01); *G01N 33/2823* (2013.01); *G01N 2223/601* (2013.01)

(58) Field of Classification Search
CPC .... G01N 23/06; G01N 23/083; G01N 23/087; G01N 23/12; G01N 2223/601; G01N 33/28; G01N 33/2823
USPC ........................................ 378/51–56, 58, 59
See application file for complete search history.

(56) References Cited

U.S. PATENT DOCUMENTS

| | | | | |
|---|---|---|---|---|
| 3,246,145 A | | 4/1966 | Higgins | |
| 4,064,440 A | | 12/1977 | Roder | |
| 4,289,020 A | | 9/1981 | Paap | |
| 4,346,599 A | | 8/1982 | McLaughlin | |
| 4,805,641 A | | 2/1989 | Radzio | |
| 4,986,285 A | | 1/1991 | Radzio | |
| 5,379,237 A | * | 1/1995 | Morgan | B21B 37/78 378/59 |
| 5,414,648 A | * | 5/1995 | Morgan | G01B 15/06 250/359.1 |
| 5,420,427 A | * | 5/1995 | Morgan | G01N 23/18 250/358.1 |
| 5,475,727 A | * | 12/1995 | Buchanan | G01T 1/40 378/53 |
| 5,654,551 A | * | 8/1997 | Watt | G01F 1/7042 250/356.1 |
| 5,689,540 A | * | 11/1997 | Stephenson | G01N 23/22 378/53 |
| 5,822,390 A | * | 10/1998 | Hewitt | G01N 23/12 378/53 |
| 5,970,116 A | | 10/1999 | Dueholm | |
| 6,265,713 B1 | * | 7/2001 | Berard | G01F 1/363 250/269.3 |

(Continued)

*Primary Examiner* — Allen C. Ho
(74) *Attorney, Agent, or Firm* — Elliott & Polasek, PLLC; Douglas H. Elliott; Nathan Q. Huynh

(57) ABSTRACT

Disclosed herein are nuclear densitometer assemblies for measuring density of fracturing fluid in a pipe, which includes a nuclear densitometer assembly that may include: a lower plate; a support post extending from the lower plate, the support post capable of supporting a portion of the pipe; an upper plate; a nuclear source coupled to the upper plate; a nuclear detector coupled to the upper plate; wherein a portion of the pipe may be capable of being disposed between the nuclear source and the nuclear detector.

19 Claims, 13 Drawing Sheets

(56) References Cited

U.S. PATENT DOCUMENTS

| | | | | |
|---|---|---|---|---|
| 6,335,959 B1 * | 1/2002 | Lynch | G01N 23/06 | 378/45 |
| 6,377,654 B1 * | 4/2002 | Willems | G01B 15/025 | 250/358.1 |
| 6,389,908 B1 * | 5/2002 | Chevalier | G01N 33/2823 | 73/861.63 |
| 6,405,604 B1 * | 6/2002 | Berard | G01F 1/74 | 73/861.04 |
| 6,600,806 B1 * | 7/2003 | Istar | G01B 15/02 | 378/58 |
| 6,640,625 B1 | 11/2003 | Goodwin | | |
| 6,879,425 B2 * | 4/2005 | Damm | G01F 23/288 | 164/454 |
| 6,925,145 B2 * | 8/2005 | Batzinger | G01N 23/04 | 378/59 |
| 7,075,062 B2 | 1/2006 | Chen et al. | | |
| 7,105,805 B2 * | 9/2006 | Berard | G01N 23/12 | 250/256 |
| 7,206,376 B2 * | 4/2007 | Fitzgerald | G01N 23/06 | 378/54 |
| 7,316,166 B2 * | 1/2008 | Atkinson | G01N 23/12 | 73/861.63 |
| 7,440,543 B2 * | 10/2008 | Morton | G01F 1/66 | 378/53 |
| 7,507,952 B2 * | 3/2009 | Groves | G01 9/24 | 250/269.1 |
| 7,542,543 B2 * | 6/2009 | Shampine | G01N 9/24 | 378/56 |
| 7,561,663 B2 * | 7/2009 | Watanabe | G01N 23/083 | 378/51 |
| 7,569,810 B1 * | 8/2009 | Troxler | G01N 23/025 | 250/269.1 |
| 7,656,997 B1 * | 2/2010 | Anjelly | G01N 23/04 | 378/59 |
| 7,676,344 B2 * | 3/2010 | Chevalier | G01F 1/56 | 702/137 |
| 7,684,540 B2 * | 3/2010 | Groves | A61B 6/4241 | 378/53 |
| 7,903,782 B2 * | 3/2011 | Groves | G01N 23/083 | 378/53 |
| 7,908,930 B2 * | 3/2011 | Xie | G01N 22/00 | 73/861.04 |
| 7,978,815 B2 * | 7/2011 | Tjugum | G01N 9/24 | 378/54 |
| 8,575,562 B2 * | 11/2013 | Wuestenbecker | G01N 23/083 | 250/393 |
| 8,718,230 B2 * | 5/2014 | Luo | G01N 33/2823 | 378/53 |
| 8,744,042 B2 * | 6/2014 | Ohzu | G01N 23/223 | 378/46 |
| 9,217,720 B2 * | 12/2015 | Prentice | G01N 23/083 | |
| 9,244,024 B1 * | 1/2016 | Patterson | G01N 23/18 | |
| 9,448,189 B2 * | 9/2016 | Korkin | G01N 23/12 | |
| 9,581,558 B2 * | 2/2017 | Cadalen | G01N 23/12 | |
| 9,869,647 B2 * | 1/2018 | Featonby | G01N 23/18 | |
| 9,874,507 B2 * | 1/2018 | Dingman | G05D 1/0011 | |
| 9,897,558 B2 * | 2/2018 | Bowdon | G01N 23/046 | |
| 10,018,748 B2 * | 7/2018 | Black | G01N 33/2847 | |
| 10,126,156 B2 * | 11/2018 | Chen | G01F 1/42 | |
| 10,309,946 B2 * | 6/2019 | Buckley | G01N 23/04 | |
| 10,429,324 B2 * | 10/2019 | Phin | G01N 23/083 | |
| 10,502,697 B2 * | 12/2019 | Georgeson | G01N 23/203 | |
| 10,533,955 B2 * | 1/2020 | Parker | G01N 9/24 | |
| 10,578,565 B2 * | 3/2020 | Safai | G01N 23/02 | |
| 10,663,412 B2 * | 5/2020 | Nguyen | G01N 15/088 | |
| 10,704,937 B2 * | 7/2020 | Chen | G01N 23/095 | |
| 10,732,131 B2 * | 8/2020 | Schmitz | G01N 23/04 | |
| 2011/0048125 A1 | 3/2011 | Jackson | | |
| 2014/0321729 A1 | 10/2014 | Gudmundson et al. | | |

* cited by examiner

US 10,890,544 B1

NUCLEAR DENSITOMETER ASSEMBLIES FOR HYDRAULIC FRACTURING

BACKGROUND

1. Field of Inventions

The field of this application and any resulting patent is nuclear densitometer assemblies, preferably for hydraulic fracturing.

2. Description of Related Art

Various nuclear densitometer assemblies and methods for measuring fluid density, preferably for hydraulic fracturing, have been proposed and utilized, including some of the methods and structures disclosed in some of the references appearing on the face of this application or issued patent. However, those methods and structures lack the combination of steps and/or features of the methods and/or structures disclosed herein. Furthermore, it is contemplated that the methods and/or structures disclosed herein solve many of the problems that prior art methods and structures have failed to solve. Also, the methods and/or structures disclosed herein have benefits that would be surprising and unexpected to a hypothetical person of ordinary skill with knowledge of the prior art existing as of the filing date of this application.

SUMMARY

The disclosure herein includes a nuclear densitometer assembly for measuring density of fracturing fluid in a pipe, which nuclear densitometer assembly may include: a lower plate; a support post extending from the lower plate, the support post capable of supporting a portion of the pipe; an upper plate; a nuclear source coupled to the upper plate; a nuclear detector coupled to the upper plate; wherein a portion of the pipe may be capable of being disposed between the nuclear source and the nuclear detector.

The disclosure herein includes a nuclear densitometer assembly for measuring density of fracturing fluid in a pipe, which nuclear densitometer assembly may include: a lower plate; a support post extending from the lower plate, the support post capable of supporting a portion of the pipe; an upper plate; a vibration dampener disposed between the lower plate and the upper plate; a nuclear source coupled to the upper plate; a nuclear detector coupled to the upper plate; wherein a portion of the pipe is capable of being disposed between the nuclear source and the nuclear detector.

The disclosure herein includes a nuclear densitometer assembly for measuring density of fracturing fluid in a pipe, which nuclear densitometer assembly may include: an upper plate; two support posts extending above the lower plate, each of the two support posts capable of supporting a portion of the pipe; a nuclear source coupled to the upper plate; a nuclear detector coupled to the upper plate; wherein a portion of the pipe may be capable of being disposed between the nuclear source and the nuclear detector.

The disclosure herein includes a nuclear densitometer assembly for measuring density of fracturing fluid in a pipe, which nuclear densitometer assembly may include: a lower plate coupled to a portion of the pipe; an upper plate disposed between the lower plate and a second portion of the pipe; a vibration dampener disposed between the lower plate and the upper plate; a first collimator; a second collimator, wherein the first collimator shares a central axis with the second collimator; a nuclear source coupled to the upper plate; and a nuclear detector coupled to the upper plate; wherein the second portion of the pipe may be disposed between the nuclear source and the nuclear detector.

The disclosure herein includes a nuclear densitometer assembly for measuring density of fracturing fluid in a pipe, which nuclear densitometer assembly may include: a first collimator with a first shield coupled to the first collimator; a second collimator with a second shield coupled to the second collimator; a nuclear source coupled to the first collimator; and a nuclear detector coupled to the second collimator; wherein the first shield may be configured to provide a first gap between the first shield and the pipe and the second shield may be configured to provide a second gap between the second shield and the pipe such that the first shield and the second shield are not capable of being in physical contact with the pipe while the fracturing fluid is passing through the pipe.

A method of measuring density of fluid in a pipe, which method may include: providing a nuclear densitometer assembly, which nuclear densitometer assembly may include: a lower plate; an upper plate; a vibration dampener disposed between the lower plate and upper plate; a first shield coupled to upper plate; a second shield coupled to upper plate; a first collimator coupled the first shield; and a second collimator coupled the second shield, wherein the first collimator may share a central axis with the second collimator; coupling a portion of a pipe to the lower plate; disposing a second portion of the pipe between the first shield, the second shield, the first collimator, and the second collimator; transmitting atomic particles or radiation from a nuclear source through the first collimator and the second collimator to the nuclear detector; and absorbing, with the vibration dampener, vibration transmitted from the pipe to the lower plate.

DETAILED DESCRIPTION

1. Introduction

Figure 1:
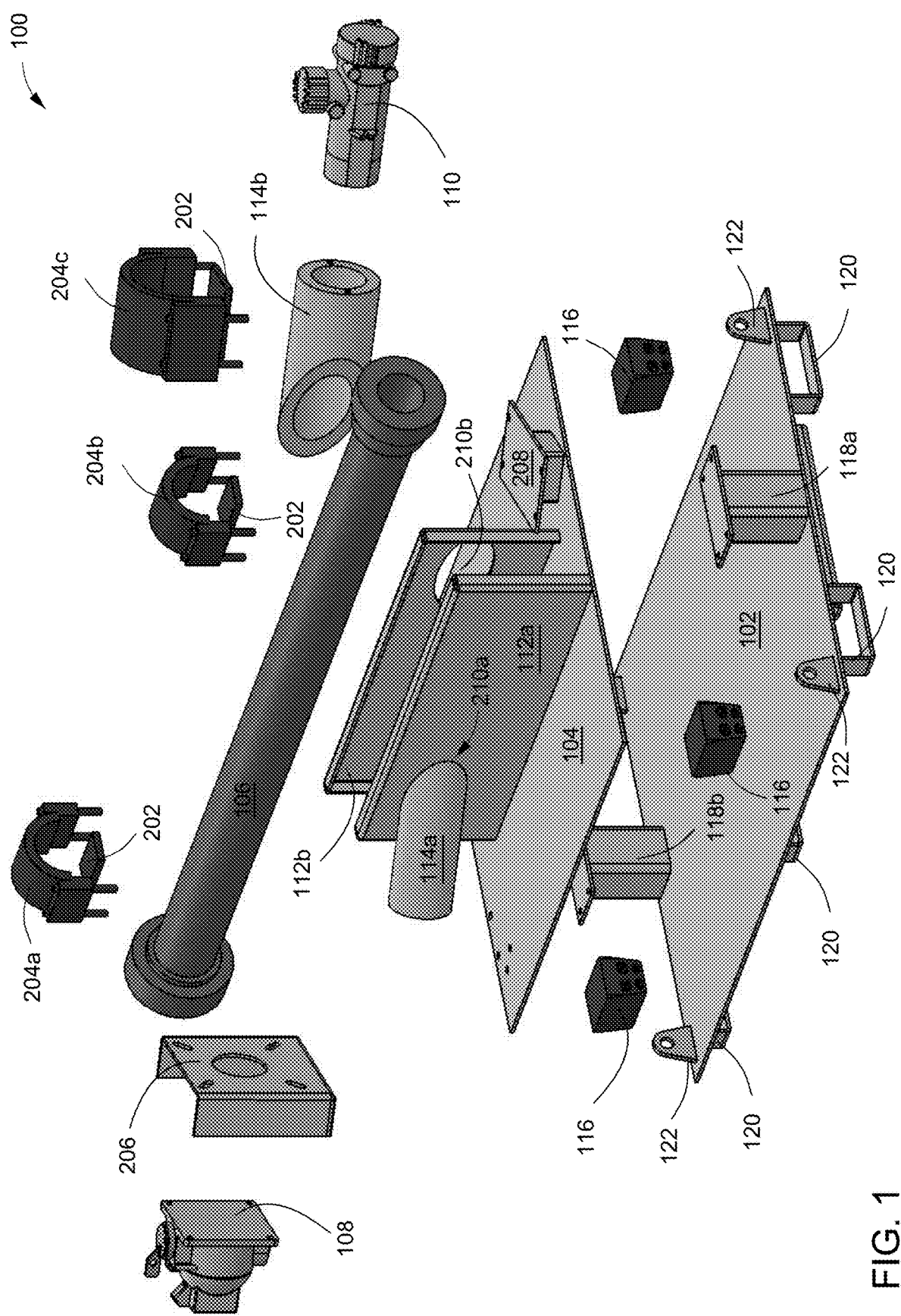
FIG. 1 illustrates an exploded view of a nuclear densitometer assembly with a frac pipe.

A detailed description will now be provided. The purpose of this detailed description, which includes the drawings, is to satisfy the statutory requirements of 35 U.S.C. § 112. For example, the detailed description includes a description of inventions defined by the claims and sufficient information that would enable a person having ordinary skill in the art to make and use the inventions. In the figures, like elements are generally indicated by like reference numerals regardless of the view or figure in which the elements appear. The figures are intended to assist the description and to provide a visual representation of certain aspects of the subject matter described herein. The figures are not all necessarily drawn to scale, nor do they show all the structural details, nor do they limit the scope of the claims.

Each of the appended claims defines a separate invention which, for infringement purposes, is recognized as including equivalents of the various elements or limitations specified in the claims. Depending on the context, all references below to the "invention" may in some cases refer to certain specific embodiments only. In other cases, it will be recognized that references to the "invention" will refer to the subject matter recited in one or more, but not necessarily all, of the claims. Each of the inventions will now be described in greater detail below, including specific embodiments, versions, and examples, but the inventions are not limited to these specific embodiments, versions, or examples, which are included to enable a person having ordinary skill in the art to make and use the inventions when the information in this patent is combined with available information and technology. Various terms as used herein are defined below, and the definitions should be adopted when construing the claims that include those terms, except to the extent a different meaning is given within the specification or in express representations to the Patent and Trademark Office (PTO). To the extent a term used in a claim is not defined below or in representations to the PTO, it should be given the broadest definition persons having skill in the art have given that term as reflected in at least one printed publication, dictionary, or issued patent.

2. Selected Definitions

Certain claims include one or more of the following terms which, as used herein, are expressly defined below.

The term "aligning" as used herein is a verb that means manufacturing, forming, adjusting, or arranging one or more physical objects into a particular position. After any aligning takes place, the objects may be fully or partially "aligned." Aligning preferably involves arranging a structure or a surface of a structure in linear relation to another structure or surface; for example, such that their borders or perimeters may share a set of parallel tangential lines. In certain instances, the aligned borders or perimeters may share a similar profile. Additionally, apertures may be aligned, such that a structure or portion of a structure may be extended into and/or through the apertures.

The term "aperture" as used herein is defined as any opening in a solid object or structure, e.g., pipe, collimator, and/or shield. For example, an aperture may be an opening that begins on one side of a solid object and ends on the other side of the object. An aperture may alternatively be an opening that does not pass entirely through an object, but only partially passes through, e.g., as a groove. An aperture can be an opening in an object that is completely circumscribed, defined, or delimited by the object itself. Alternatively, an aperture can be an opening formed when one object is combined with one or more other objects or structures. An aperture may receive an object, e.g., nuclear particles.

The term "assembly" as used herein is defined as any set of components that have been fully or partially assembled together. A group of assemblies may be coupled to form a solid housing having an inner surface and an outer surface.

The term "collimator" as used herein is defined as an elongated structure configured for narrowing a path of travel of nuclear particles therethrough. A collimator may extend in any direction but preferably in a direction oblique to the central axis of a pipe. A collimator may alternatively extend in a direction perpendicular to the central axis of a pipe. A collimator may extend from a shield as exemplified in the drawings. A collimator may extend from a shield in an oblique direction as also shown in the drawings.

The term "clamp" as used herein is defined as an assembly capable of being removably coupled to another object using pressure. Parts of a clamp may be pressed against a pipe and/or a support post. A clamp is capable of being removably coupled to a pipe and/or a support post. A clamp may have a body, a first terminal, and a second terminal. A clamp may have a body, a first terminal, and a second terminal that are a unitary single molded rigid piece. A clamp may have two portions coupled together around a structure, e.g., pipe and/or vibration dampener. A clamp may be molded, 3D-printed, or carved from a single piece of material, e.g., plastic, carbon fiber, metal, or wood. A clamp may have a body capable of being abutted against a pipe. A clamp may have the shape of a block-letter "C" or "G." A clamp may be a G-clamp, a C-clamp, a clip, a latch, a hook, fasteners, or a lock. A clamp may have two C-shaped portions coupled together to form an aperture extending through the two C-shaped portion, e.g., forming a block-letter "O." A clamp may include one or more bolts extending therethrough. The one or more bolts may be threadably coupled to a support post or a lower plate. A clamp may include more bolts extending through terminals of the clamp. The bolts may be threadably coupled to a lower plate, an upper plate, or a support post.

The term "coupled" as used herein is defined as directly or indirectly connected or attached. A first object may be coupled to a second object such that the first object is positioned at a specific location and orientation with respect to the second object.

The term "cylindrical" as used herein is defined as shaped like a cylinder, e.g., having straight parallel sides and a circular or oval or elliptical cross-section. Examples of a cylindrical structure or object include a pipe and a collimator. A cylindrical object may be completely or partially shaped like a cylinder. For example, a cylindrical object may have an aperture that is extended through the entire length of the housing to form a hollow cylinder capable of permitting another object, e.g., pipe or collimator, to be extended or passed through. Alternatively, a solid cylindrical object may have an inner surface or outer surface having a diameter that changes abruptly. A cylindrical object may have and inner or outer surface having a diameter that changes abruptly to form a collar, e.g., radial face, rim, or lip. A cylindrical object may have a collar extending toward or away from the central axis line of the object. A cylindrical object may have a collar disposed on an inner surface. A cylindrical object may have a collar disposed on an outer surface. Additionally, a cylindrical object, may have a collar that is tapered or radiused.

The terms "first" and "second" as used herein merely differentiate two or more things or actions, and do not signify anything else, including order of importance, sequence, etc.

The term "flow rate" as used herein is defined as the volume of material or fluid that passes per unit of time. Volume may be measured in gallons or liters, for example. Time may be measured in seconds, minutes, or hours, for example. A flow rate of a pumped fluid may be measured at the surface or at any other location. A flow rate of a pumped fluid may be measured at any time, including before the fluid is pumped into a downhole pipe. A flow rate of a pumped fluid may be measured at a station or a pump that pumped the fluid. A "fluid flow rate" may range from as low as 30, 35, 40, 45, 50, 55, 60, or 70 gallons per minute to 80, 90, 120, 130, 140, 160, 200, or 250 gallons per minute or higher.

The term "fluid" as used herein is defined as material that is capable of being flowed. A fluid may be a liquid or a gas. Examples of a fluid may include hydrocarbon, water, saltwater, brine, cement, lubricant, cleaning fluid, and motor oil. A fluid may include material, e.g., pounds proppant additive (PPA), slurry, coated sand, sand, hydrocarbon, water, compounds, and/or elements originating from underground rock formation. A fluid can be a mixture of two or more fluids. A fluid may absorb heat. A fluid may have properties such as viscosity, anti-foaming, thermal stability, thermal conductivity, and thermal capacity.

The term "impact" as used herein as a noun is defined as forcible contact of a first object against a second object. Forcible contact may result from between two objects. For example, a person swinging a hammer against a pipe may impart impact against the pipe. In another example, during transit, a vehicle bed may impart impact on a nuclear densitometer assembly. An object receiving impact may be vibrated.

The term "nuclear densitometer assembly" as used herein is defined as an assembly or structure that includes a nuclear densitometer, including any well-known or conventional device that is capable of measuring the density of fluid, particularly a fluid flowing through a pipe, e.g., an apparatus that measures density of a fluid using nuclear particles. A nuclear densitometer assembly may include one or more plates, one or collimators, a support post, a nuclear source, a nuclear detector, vibration dampeners, pipe supports, and/or clamps.

The term "path" as used herein is defined as a space through which fluid, particles, and/or energy may travel. A path may be disposed within an object, e.g., pipe. A path may extend uninterrupted from one end of an object to another, e.g., through a pipe from one end to another. A path may be formed by a groove disposed on an object. A path may be a groove disposed in an outer surface of an object. A path may be formed by the inner surface of an object. A path may be formed by the inner surface of a group of coupled objects, e.g., pipes or pipe couplings. A path may be formed from two or more connected paths. The term "flow path" as used herein is defined as a space through which fluid is capable of flowing, e.g., through a conduit. The term "nuclear path" as used herein is defined as a space through which radioactive particles or radioactive energy, e.g., radiation, may be transmitted. For example, a collimator may provide a nuclear path for transmission of radioactive particles and/or radiation, e.g., from a nuclear source to a nuclear detector.

The term "perpendicular" as used herein is defined as at an angle ranging from a low of 85° to 88 to a high of 92° to 95°. Two structures that are perpendicular to each other may be orthogonal and/or tangential to each other.

The term "plate" as used herein refers to any structure that includes a flat surface. The plate may be constructed of any material, including metal, plastic, or carbon fiber. A plate may have an upper surface and a lower surface.

The term "pressure" as used herein is defined as applied, e.g., force per unit area. Pressure may be exerted against a surface of an object, e.g., pipe, support post, and/or vibration dampener.

The term "providing" as used herein is defined as making available, furnishing, supplying, equipping, or causing to be placed in position.

The term "pipe" as used herein is defined as a structure having an inner surface and an outer surface and an inner space that is preferably a conduit that extends from one end to another end. A pipe may have a through-bore, e.g., aperture. Preferably, a pipe may be cylindrical. Preferably, a pipe is configured to receive fluid, e.g., hydrocarbon, water, cement, lubricant, and/or cleaning fluid. Any or all pipes of an assembly may have polygonal cross-sections, e.g., triangular, rectangular, pentagonal, hexagonal, or octagonal.

The term "shield" as used herein refers to any structure, preferably, a plate with a flat surface, that is parallel to the flow path of the fluid, e.g., the fracturing fluid, and is preferably perpendicular to upper or lower plates that are positioned below the pipe. A nuclear densitometer assembly preferably includes at least one plate on one side of the pipe closer to the nuclear source and another plate on the other side of the pipe closer to the nuclear detector. A shield may be configured to inhibit movement of nuclear particles and/or transmission of radioactive energy.

The term "surface" as used herein is defined as any face of a structure. A surface may also refer to that flat or substantially flat area that is extended radially around a cylinder which may, for example, be part of a collimator, a pipe, vibration dampener, or a seal. A surface may have irregular contours. A surface may be formed from components, e.g., plates, feet, channels, brackets and/or collimators, coupled together. Coupled components may form irregular surfaces.

The term "vibration" as used herein is defined as disturbance, including oscillation of one or more portions of a fluid or solid, e.g., pup, base, or support post.

The term "vibration dampener" as used herein is defined as a structure configured to either absorb and/or reduce vibration and/or impact. A vibration dampener may be elastic and/or resilient. A vibration dampener may be constructed from one or more elastomers, e.g., rubber, silicone, acrylic, butadiene, butyl, chlorinated polyethylene, ethylene propylene, fluorocarbon, isoprene, nitrile, polysulphide, polyurethane, urethane, styrenic block copolymer, copolyether ester, and polyester amide.

3. Certain Specific Embodiments

The disclosure herein includes a nuclear densitometer assembly for measuring density of fracturing fluid in a pipe, which nuclear densitometer assembly may include: a lower plate; a support post extending from the lower plate, the support post capable of supporting a portion of the pipe; an upper plate; a nuclear source coupled to the upper plate; a nuclear detector coupled to the upper plate; wherein a portion of the pipe may be capable of being disposed between the nuclear source and the nuclear detector.

The disclosure herein includes a nuclear densitometer assembly for measuring density of fracturing fluid in a pipe, which nuclear densitometer assembly may include: a lower plate; a support post extending from the lower plate, the support post capable of supporting a portion of the pipe; an upper plate; a vibration dampener disposed between the lower plate and the upper plate; a nuclear source coupled to the upper plate; a nuclear detector coupled to the upper plate; wherein a portion of the pipe is capable of being disposed between the nuclear source and the nuclear detector.

The disclosure herein includes a nuclear densitometer assembly for measuring density of fracturing fluid in a pipe, which nuclear densitometer assembly may include: an upper plate; two support posts extending above the lower plate, each of the two support posts capable of supporting a portion of the pipe; a nuclear source coupled to the upper plate; a nuclear detector coupled to the upper plate; wherein a portion of the pipe may be capable of being disposed between the nuclear source and the nuclear detector.

The disclosure herein includes a nuclear densitometer assembly for measuring density of fracturing fluid in a pipe, which nuclear densitometer assembly may include: a lower plate coupled to a portion of the pipe; an upper plate disposed between the lower plate and a second portion of the pipe; a vibration dampener disposed between the lower plate and the upper plate; a first collimator; a second collimator, wherein the first collimator shares a central axis with the second collimator; a nuclear source coupled to the upper plate; and a nuclear detector coupled to the upper plate; wherein the second portion of the pipe may be disposed between the nuclear source and the nuclear detector.

The disclosure herein includes a nuclear densitometer assembly for measuring density of fracturing fluid in a pipe, which nuclear densitometer assembly may include: a first collimator with a first shield coupled to the first collimator; a second collimator with a second shield coupled to the second collimator; a nuclear source coupled to the first collimator; and a nuclear detector coupled to the second collimator; wherein the first shield may be configured to provide a first gap between the first shield and the pipe and the second shield may be configured to provide a second gap between the second shield and the pipe such that the first shield and the second shield are not capable of being in physical contact with the pipe while the fracturing fluid is passing through the pipe.

A method of measuring density of fluid in a pipe, which method may include: providing a nuclear densitometer assembly, which nuclear densitometer assembly may include: a lower plate; an upper plate; a vibration dampener disposed between the lower plate and upper plate; a first shield coupled to upper plate; a second shield coupled to upper plate; a first collimator coupled the first shield; and a second collimator coupled the second shield, wherein the first collimator may share a central axis with the second collimator; coupling a portion of a pipe to the lower plate; disposing a second portion of the pipe between the first shield, the second shield, the first collimator, and the second collimator; transmitting atomic particles or radiation from a nuclear source through the first collimator and the second collimator to the nuclear detector; and absorbing, with the vibration dampener, vibration transmitted from the pipe to the lower plate.

In any one of the structures or methods disclosed herein, the lower plate may include one or more feet.

In any one of the structures or methods disclosed herein, the lower plate may include one or more feet extending from a lower surface of the lower plate.

In any one of the structures or methods disclosed herein, the lower plate may include one or more lift brackets.

In any one of the structures or methods disclosed herein, the lower plate may include one or more lift brackets extending from an upper surface of the lower plate.

Any one of the structures or methods disclosed herein may further include a clamp capable of being coupled to the support post.

Any one of the structures or methods disclosed herein may further include a clamp capable of being coupled to a portion of the pipe.

Any one of the structures or methods disclosed herein may further include a support pad capable of being disposed between a portion of the pipe and the support post.

Any one of the structures or methods disclosed herein may further include a support pad capable of being abutted against the portion of the pipe and the support post.

Any one of the structures or methods disclosed herein may further include a support pad comprising from an elastomer.

In any one of the structures or methods disclosed herein, the central axis of the pipe may be oblique to a nuclear path capable of being generated by the nuclear source.

In any one of the structures or methods disclosed herein, the central axis of the pipe may be capable of being oblique to an open path between the nuclear source and the nuclear detector.

In any one of the structures or methods disclosed herein, the nuclear detector may be capable of detecting particles or radioactive energy emitted by the nuclear source.

Any one of the structures or methods disclosed herein may further include: a first collimator; a second collimator, wherein the first collimator may share a central axis with the second collimator; a first shield having an aperture aligned with an opening of the first collimator; and a second shield having an aperture aligned with an opening of the second collimator; wherein the aperture of the first shield and the aperture of the second shield may be aligned.

Any one of the structures or methods disclosed herein may further include: a collimator having a central axis; and a shield having a plane oblique to the central axis.

Any one of the structures or methods disclosed herein may further include: a first collimator; a second collimator, wherein the first collimator may share a central axis with the second collimator; a first shield having an aperture aligned with an end of the first collimator; and a second shield having an aperture aligned with an end of the second collimator, wherein the aperture of the first shield and the aperture of the second shield may be aligned.

Any one of the structures or methods disclosed herein may further include: a first collimator; a second collimator, wherein the first collimator may share a central axis with the second collimator; and a shield disposed between the first collimator and the second collimator, wherein the shield may have a plane oblique to the central axis.

In any one of the structures or methods disclosed herein, the vibration dampener may include an elastomer.

In any one of the structures or methods disclosed herein, the upper plate does not physically touch the pipe.

In any one of the structures or methods disclosed herein, the pipe, in some cases, may not physically touch either of the first collimator or the second collimator.

In any one of the structures or methods disclosed herein, the support post may have a clamp removably coupled to a portion of the pipe.

Any one of the structures or methods disclosed herein may further include a support pad abutted against a portion of the pipe.

Any one of the structures or methods disclosed herein may further include a support pad disposed between a portion of the pipe and the lower plate.

In any one of the structures or methods disclosed herein, a central axis of the pipe may be oblique to a direct path between the nuclear source and the nuclear detector.

In any one of the structures or methods disclosed herein, the first collimator may share a central axis with the second collimator, wherein the central axis is oblique to a central axis of the pipe.

In any one of the structures or methods disclosed herein, the first collimator may share a central axis with the second collimator, wherein the central axis may intersect a central axis of the pipe at an oblique angle.

Any one of the structures or methods disclosed herein may further include a shield having a plane oblique to a central axis of the first collimator and the second collimator and parallel to a central axis of the pipe.

Any one of the structures or methods disclosed herein may further include a shield disposed between the first collimator and the second collimator, wherein the shield may have a plane oblique to the collimator and the second collimator and parallel to a portion of the pipe.

Any one of the methods disclosed herein may further include disposing a portion of the pipe on a support pad.

Any one of the methods disclosed herein may further include clamping a portion of the pipe to the support post.

Any one of the methods disclosed herein may further include transmitting atomic particles or radiation on a path intersecting a central axis of the pipe.

Any one of the methods disclosed herein may further include transmitting atomic particles or radiation on a path oblique to a central axis of the pipe.

4. Specific Embodiments in the Drawings

The drawings presented herein are for illustrative purposes only and do not limit the scope of the claims. Rather, the drawings are intended to help enable one having ordinary skill in the art to make and use the claimed inventions.

This section addresses specific versions of nuclear densitometer assemblies shown in the drawings, which relate to assemblies, elements and parts that can be part of a nuclear densitometer assembly, and methods for measuring fluid density for hydraulic fracturing. Although the methods, structures, elements, and parts described herein have been described in detail, it should be understood that various changes, substitutions, and alterations can be made without departing from the spirit and scope of the inventions as defined by the following claims. Those skilled in the art may be able to study the preferred embodiments and identify other ways to practice the inventions that are not exactly as described herein. It is the intent of the inventors that variations and equivalents of the inventions are within the scope of the claims, while the description, abstract and drawings are not to be used to limit the scope of the inventions. The inventions are specifically intended to be as broad as the claims below and their equivalents.

FIG. 1 illustrates an exploded view of a nuclear densitometer assembly 100 with a pipe 106. The nuclear densitometer assembly 100 may include a lower plate 102, an upper plate 104, a nuclear source 108, a nuclear detector 110, shields 112a, 112b, collimators 114a, 114b, and one or more vibration dampeners 116. The pipe 106 may be a portion of a longer pipe string (not shown). The pipe string may extend downhole into the earth.

The lower plate 102 may include one or more support posts 118 and feet 120, preferably four feet adjacent the four corners of the lower plate 102 The lower plate 102 may have an upper surface and a lower surface. Four feet 120 may be couple to the lower surface of the lower plate 102. In some versions, the lower plate 102 may have two elongated feet 120, e.g., channels, on opposing edges of the lower plate 102. The one or more support posts 118 may extend from the upper surface of the lower plate 102. The one or more support posts 118 may be coupled to upper surface of the lower plate 102. Each support post 118 may be disposed near the midpoint of an edge of the lower plate 102. In some cases, the one or more support posts 118 may not physically touch the upper plate 104, e.g., so that there is a gap between each support post 118 and the upper plate 104. Also, lift brackets 122 may be coupled to the upper surface of the lower plate 102.

If the nuclear densitometer assembly 100 is required to be lifted or repositioned, the feet 120 and/or the lift brackets 122 could be used. Cables from a hoist or a crane may be coupled to the lift brackets 122. An operator may cause the hoist or the crane to lift the nuclear densitometer assembly 100. Alternatively, the operator may operate a forklift and extend tines of a forklift through the feet 120, under lower plate 102. The operator may operate the forklift to move the nuclear densitometer assembly 100.

Figure 2:
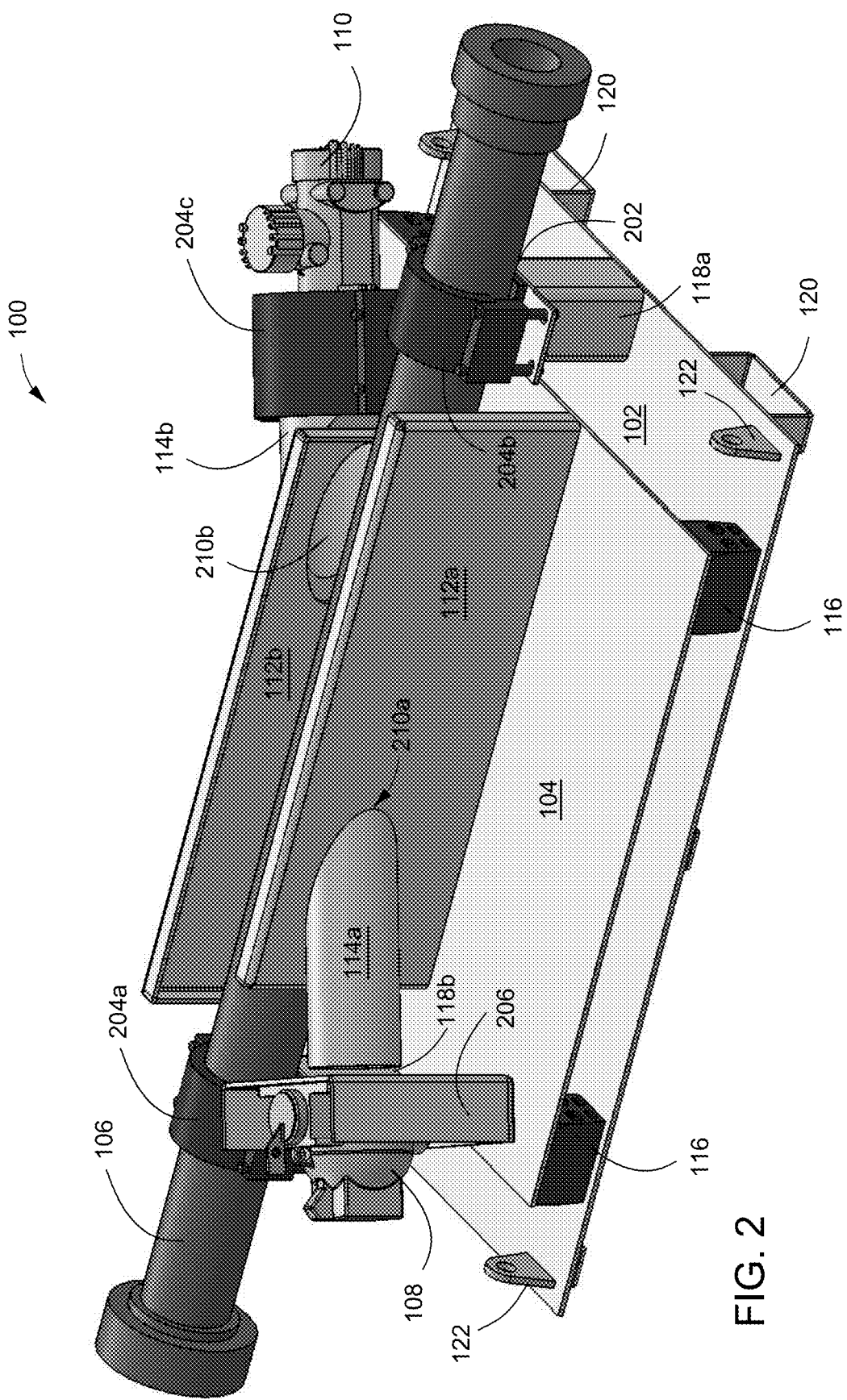
FIG. 2 illustrates a perspective view of a nuclear densitometer assembly with a frac pipe.
Figure 3:
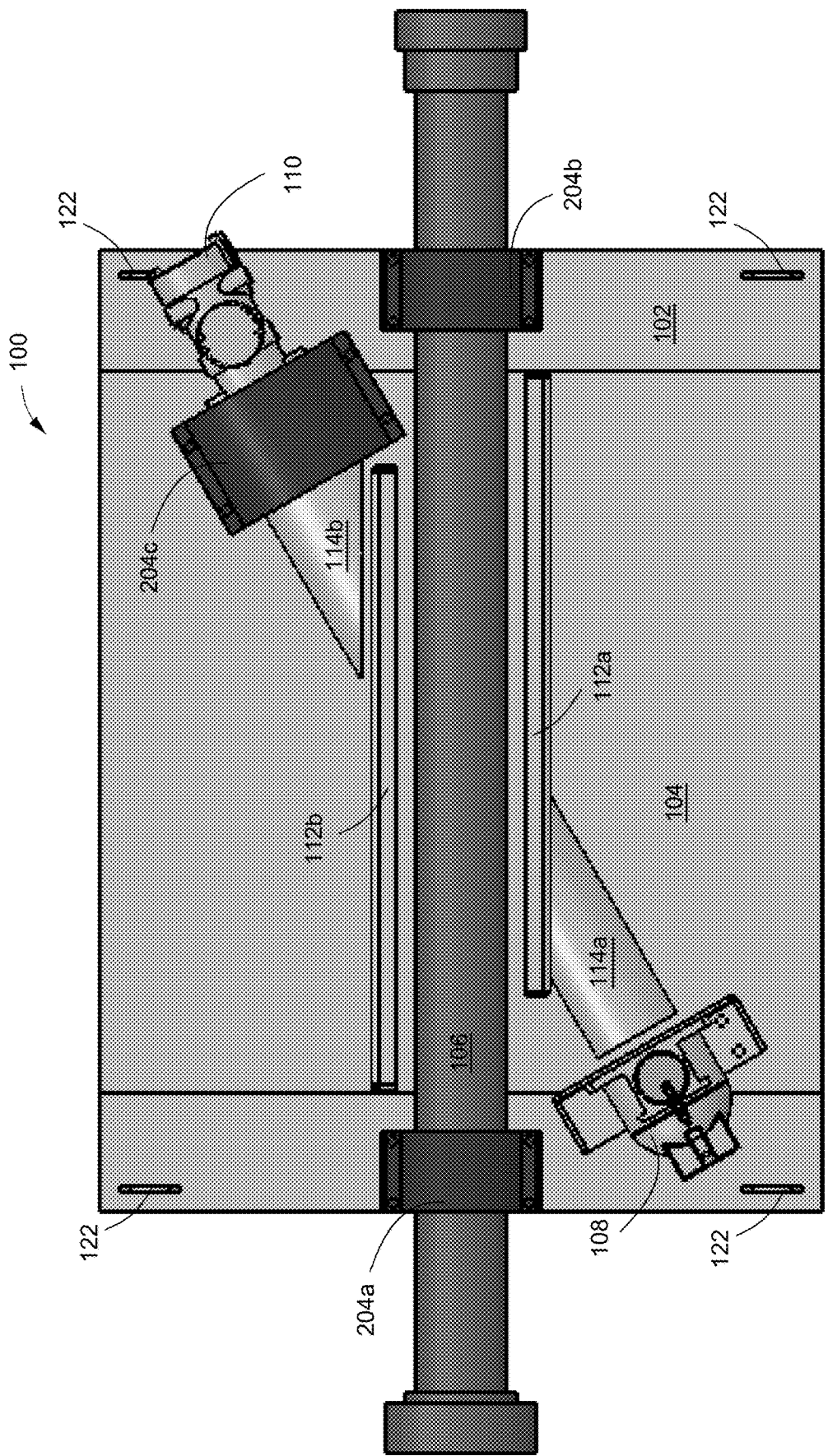
FIG. 3 illustrates a top plan view of a nuclear densitometer assembly with a frac pipe.

Referring to FIG. 2 and FIG. 3, the nuclear densitometer assembly 100 may include a lower plate 102, an upper plate 104, a nuclear source 108, a nuclear detector 110, shields 112a, 112b, collimators 114a, 114b, and one or more vibration dampeners 116. The pipe 106 may be mounted on support posts 118a, 118b. Additionally, support pads 202 may be disposed between portions of the pipe 106 and the support posts 118a, 118b. Clamps 204a, 204b may be mounted on the portions of the pipe 106. In addition, the clamps 204a, 204b may be coupled, e.g., via bolts, to the support posts 118a, 118b, respectively.

Vibration dampeners 116 may be disposed between the lower plate 102 and the upper plate 104. The vibration dampeners 116 may be disposed between an upper surface of the lower plate 102 and a lower surface of the upper plate 104. The vibration dampeners 116 may be coupled to an upper surface of the lower plate 102. Additionally, the vibration dampeners 116 may be coupled to the upper plate 104.

The upper plate 104 may have the shields 112a, 112b, a source bracket 206, and a collimator support post 208 coupled to the upper surface of the upper plate 104 (see FIG. 1).

The first collimator 114a may be positioned at an oblique angle to the shield 112a. An inner bore of the first collimator 114a may be aligned, e.g., concentric, with an aperture 210a of the shield 112a. The first collimator 114a may be coupled to the shield 112a.

The nuclear source 108 may be coupled to the source bracket 206. The nuclear source 108 may be aligned with the inner bore of the first collimator 114a such that nuclear particles or radiation, when emitted from the nuclear source 108, would travel through the inner bore.

The second collimator 114b may be coupled to the collimator support post 208. A clamp 204c may be coupled to a portion of the second collimator 114b. In addition, the clamp 204c may be coupled, e.g., via bolts, to the collimator support post 208. The second collimator 114b may be positioned at an oblique angle to the shield 112b. The nuclear detector 110 may be coupled to the second collimator 114b. The nuclear detector 110 may be aligned with the inner bore of the second collimator 114b such that nuclear particles or radiation travelling through the second collimator 114b is detectable by the nuclear detector 110.

The inner bore of the second collimator 114b may be aligned with an aperture 210b disposed through the shield 112b. The inner bore of the first collimator 114a, the inner bore of the second collimator 114b, and the apertures 210a, 210b may be aligned. In other words, the inner bore of the first collimator 114a, the inner bore of the second collimator 114b, and the apertures 210a, 210b may share a central axis. Thus, after being emitted from the nuclear source 108, nuclear particles or radiation would travel through the inner bore of the first collimator 114a, the aperture 210a of the shield 112a, the pipe 106, the aperture 210b of the shield 112b, and the inner bore of the second collimator 114b to the nuclear detector 110.

Figure 4A:
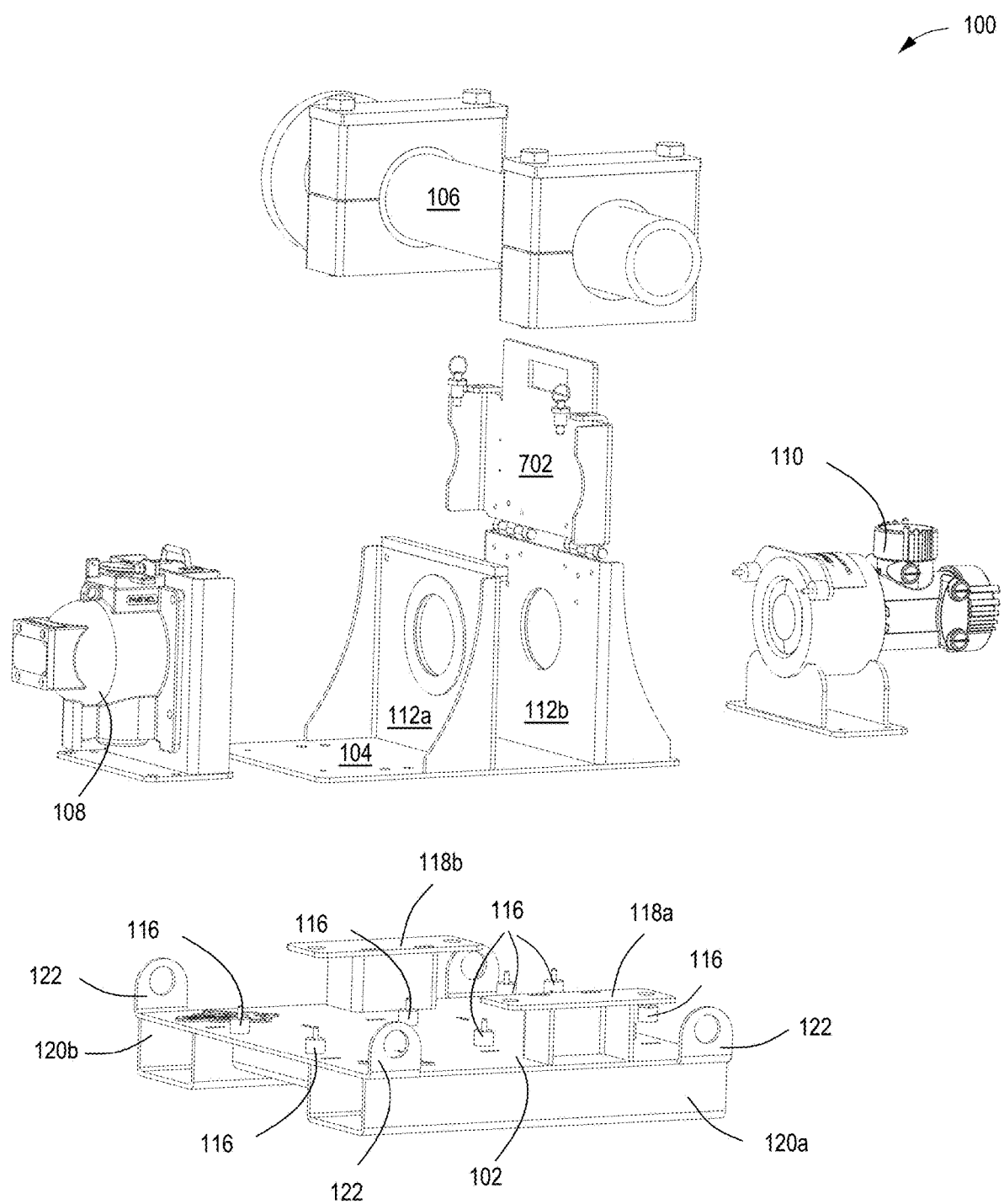
FIG. 4A illustrates an exploded view of another version of a nuclear densitometer assembly with a pipe.
Figure 4B:
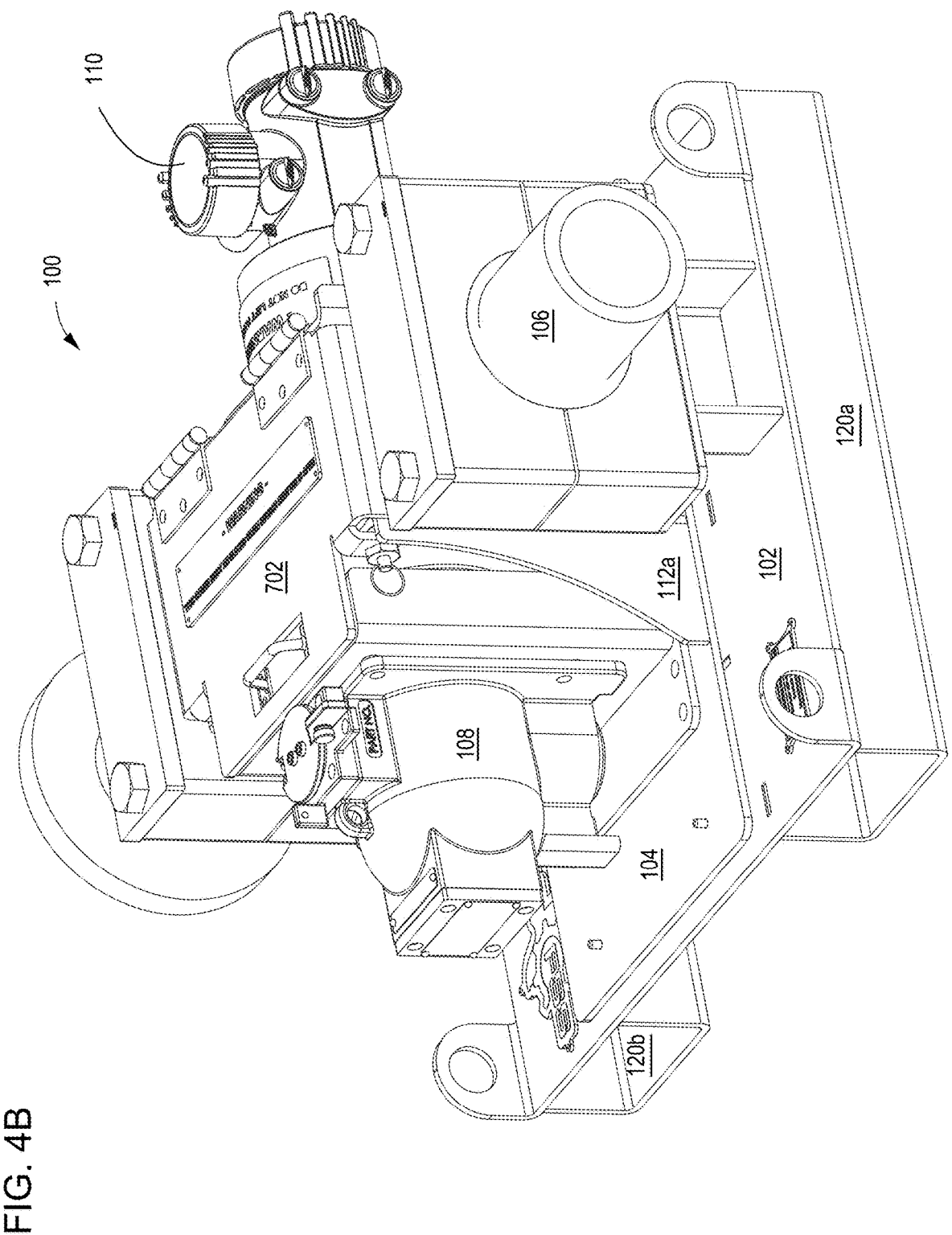
FIG. 4B illustrates a perspective view of another version of a nuclear densitometer assembly assembled.
Figure 4C:
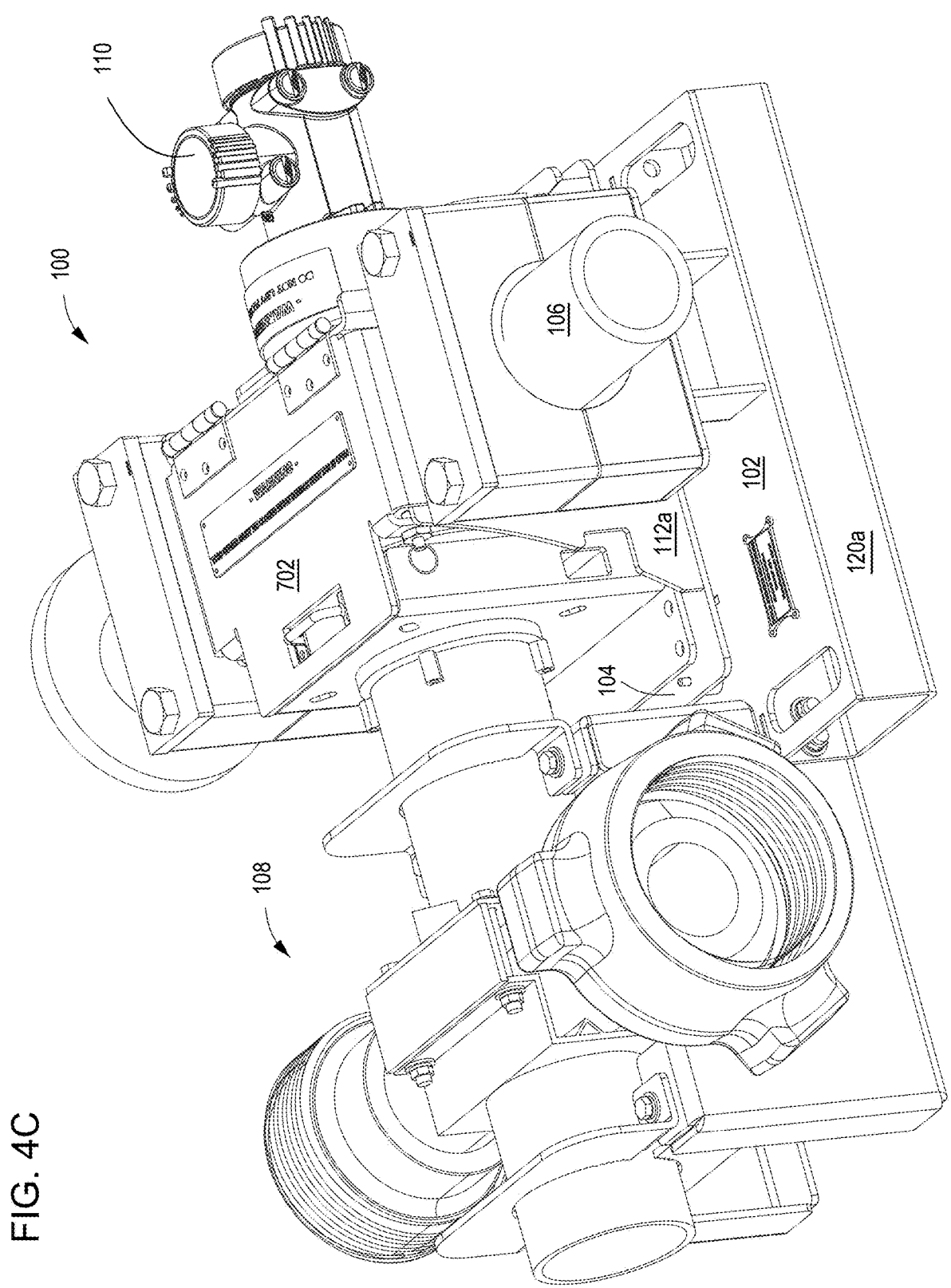
FIG. 4C illustrates a perspective view of a nuclear densitometer assembly assembled including an alternate nuclear source.

FIG. 4A illustrates an exploded view of another version of a nuclear densitometer assembly 100 with a pipe 106. FIG. 4B illustrates a perspective view of another version of a nuclear densitometer assembly 100 assembled. FIG. 4C illustrates a perspective view of a nuclear densitometer assembly assembled including an alternate nuclear source.

Referring to FIGS. 4A-C, a nuclear densitometer assembly 100 may include a lower plate 102, an upper plate 104, a nuclear source 108, a nuclear detector 110, shields 112a, 112b, and one or more vibration dampeners 116. The pipe 106 may be a portion of a longer pipe string (not shown). The pipe string may extend downhole into the earth.

The lower plate 102 may have an upper surface and a lower surface. The lower plate 102 may have feet 120a, 120b coupled thereto. The feet 120a, 120b may be couple to the lower surface. Accordingly, the feet 120a, 120b may extending from the lower surface, away from the upper surface. The feet 120a, 120b may be adjacent respective edges of the lower plate 102. The feet 120 may be elongated channels coupled to opposing sides of the lower plate 102. Additionally, one or more channels may be disposed between the free 120. The one or more channels may be perpendicular to the feet 120.

Also, the lower plate 102 may have support posts 118a, 118b coupled thereto. The support posts 118a, 118b may be coupled to the upper surface of the lower plate 102. The support posts 118a, 118b may extend from the upper surface of the lower plate 102, away from the lower surface of the lower plate 102. Each support post 118 may be disposed near the midpoint of an edge of the lower plate 102. Also, lift brackets 122 may be coupled to the upper surface of the lower plate 102.

The lower plate 102 may be coupled, e.g. via bolts, to the upper plate 104. Vibration dampeners 116 may be disposed between the lower plate 102 and the upper plate 104. The vibration dampeners 116 may be disposed between an upper surface of the lower plate 102 and a lower surface of the upper plate 104.

Also, the upper plate 104 may be disposed between the support posts 118a, 118b. In some cases, the support posts 118a, 118b may not physically touch the upper plate 104, e.g., so that there is space between the support posts 118a, 118b and the upper plate 104.

The upper plate 104 may have a nuclear source 108, a nuclear detector 110, and a first shield 112a, and a second shield 112b coupled thereto. The nuclear source 108 may be disposed adjacent the first shield 112a. The nuclear detector 110 may be disposed adjacent the second shield 112b. Moreover, the nuclear detector 110 may have a "line-of-sight" to the nuclear source 108, in which the nuclear detector 110 may detect nuclear particles or radiation emitted from the nuclear source 108. The "line-of-sight" between the nuclear source 108 and the nuclear detector 110 may be perpendicular to the shields 112a, 112b.

Components and structures of the nuclear densitometer assembly 100 of FIGS. 4A-B are discussed below in greater detail, in relation to the views of FIGS. 5-8.

Figure 5A:
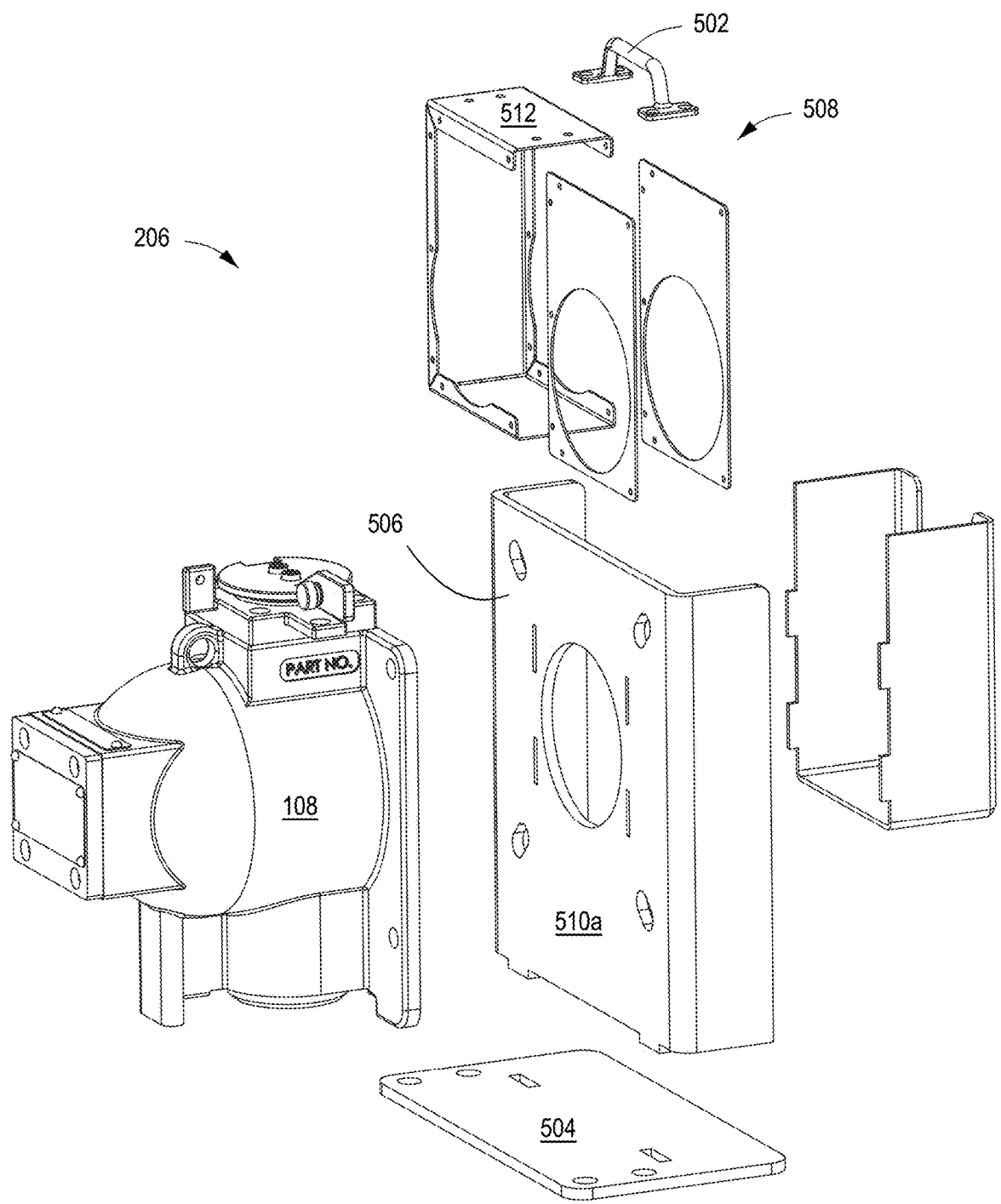
FIG. 5A illustrates an exploded view of a nuclear source, a source bracket, and a latch.
Figure 5B:
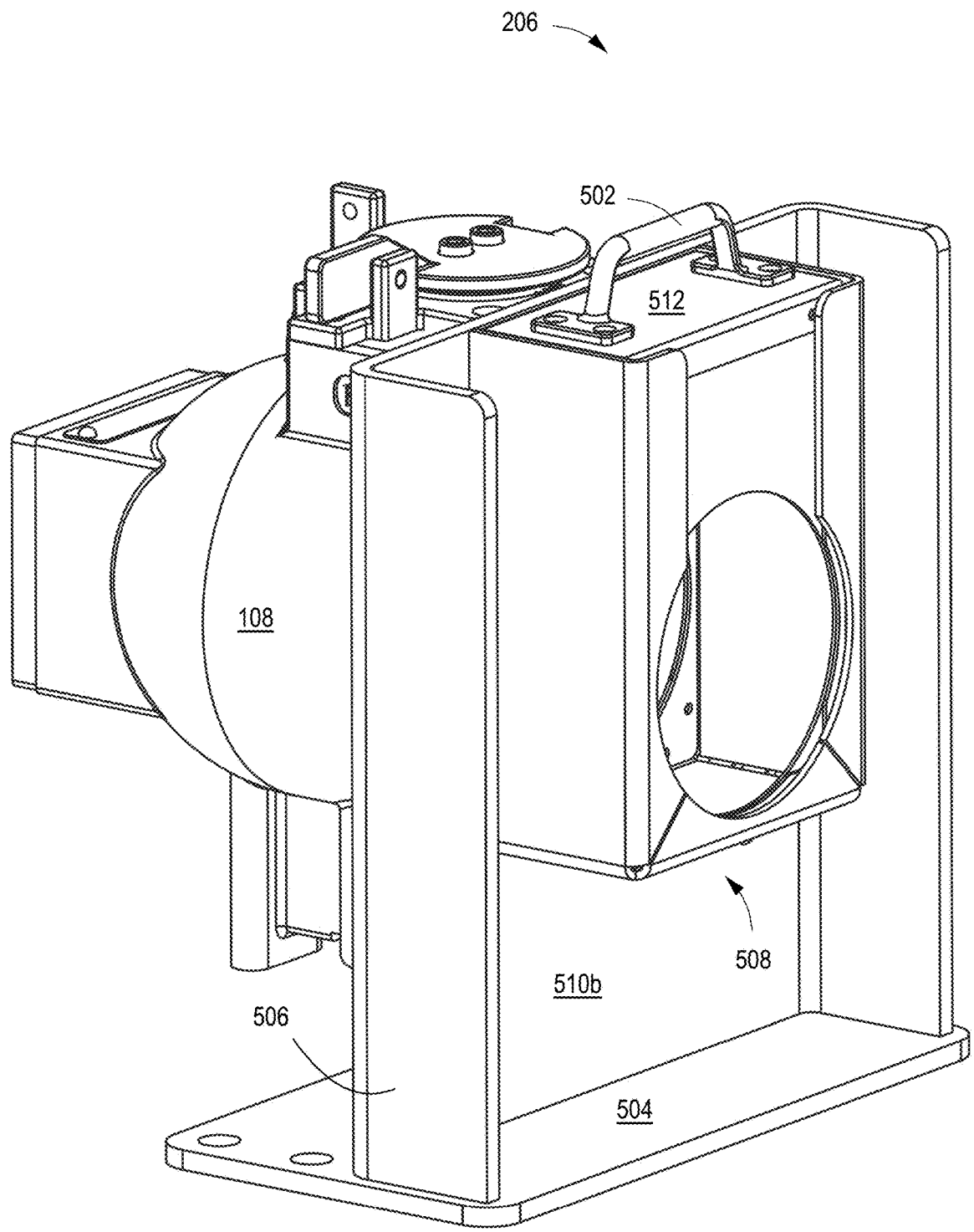
FIG. 5B illustrates a perspective view of a nuclear source, a source bracket, and a latch assembled.

FIG. 5A illustrates an exploded view of a nuclear source 108, a source bracket 206, and a latch 502. FIG. 5B illustrates a perspective view of a nuclear source 108, a source bracket 206, and a latch 502 assembled.

Referring to FIGS. 5A-B, the source bracket 206 may have several plates coupled together, e.g., via bolts and/or welding, to form the source bracket 206. For example, the source bracket 206 may include a base plate 504, a mounting plate 506, and a second bracket 508. The base plate 504 may be a flat and/or planar. The mounting plate 506 may be a flat plate having end-portions bent at approximately 90 degrees, forming three continuous walls. The three walls may form a block-letter C. The base plate 504 and the mounting plate 506 may be coupled, e.g., via welding or bolts.

The base plate 504 may be coupled to the upper base 104. Accordingly, the source bracket 206 may be coupled to the upper base 104 (see FIG. 4B).

The mounting plate 506 may have a first vertical surface 510a and a second vertical surface 510b. The first vertical surface 510a and the second vertical surface 510b may be opposite sides of the mounting plate 506. The nuclear source 108 may be coupled, e.g., via bolts, to the first vertical surface 510a.

The second bracket 508 may be coupled to the second vertical surface 510b of the mounting plate 506. The second bracket 508 may be disposed opposite the nuclear source 108. The second bracket may include an upper plate 512. The upper plate 512 may be perpendicular to the support plate 506. A latch 502 may be coupled to the upper plate 512, e.g., via welding or bolts.

In some versions, the mounting plate 506 and the upper plate 512 may be unitary. The upper plate 512 may be disposed at an upper edge of the mounting plate 506. Moreover, the upper plate 512 may be an upper end-portion bent at approximately 90 degrees to the vertical surfaces 510a, 510b. Likewise, a latch 502 may be coupled to the upper plate 512, e.g., via welding or bolts.

Figure 6A:
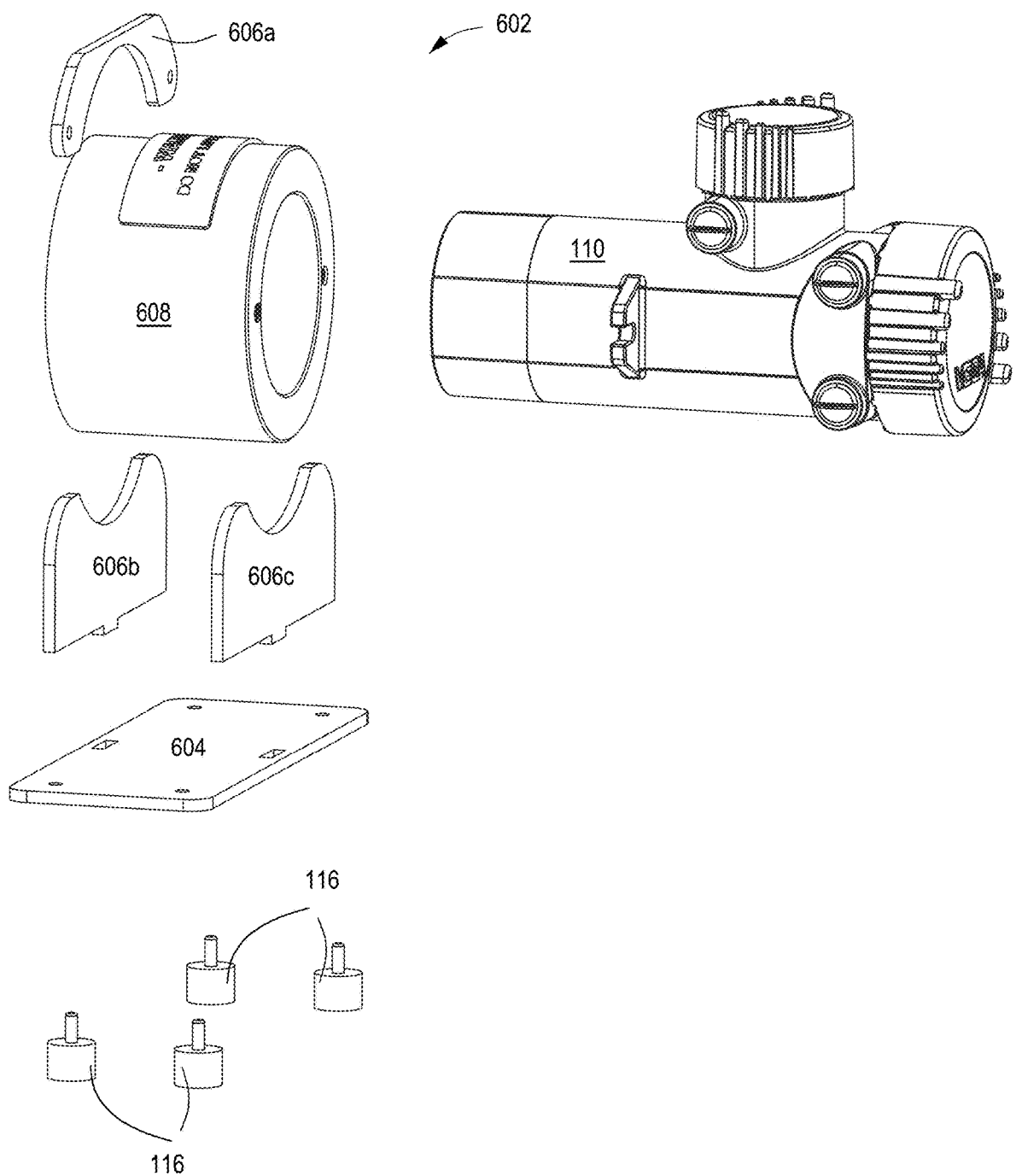
FIG. 6A illustrates an exploded view of a nuclear detector and a detector bracket.
Figure 6B:
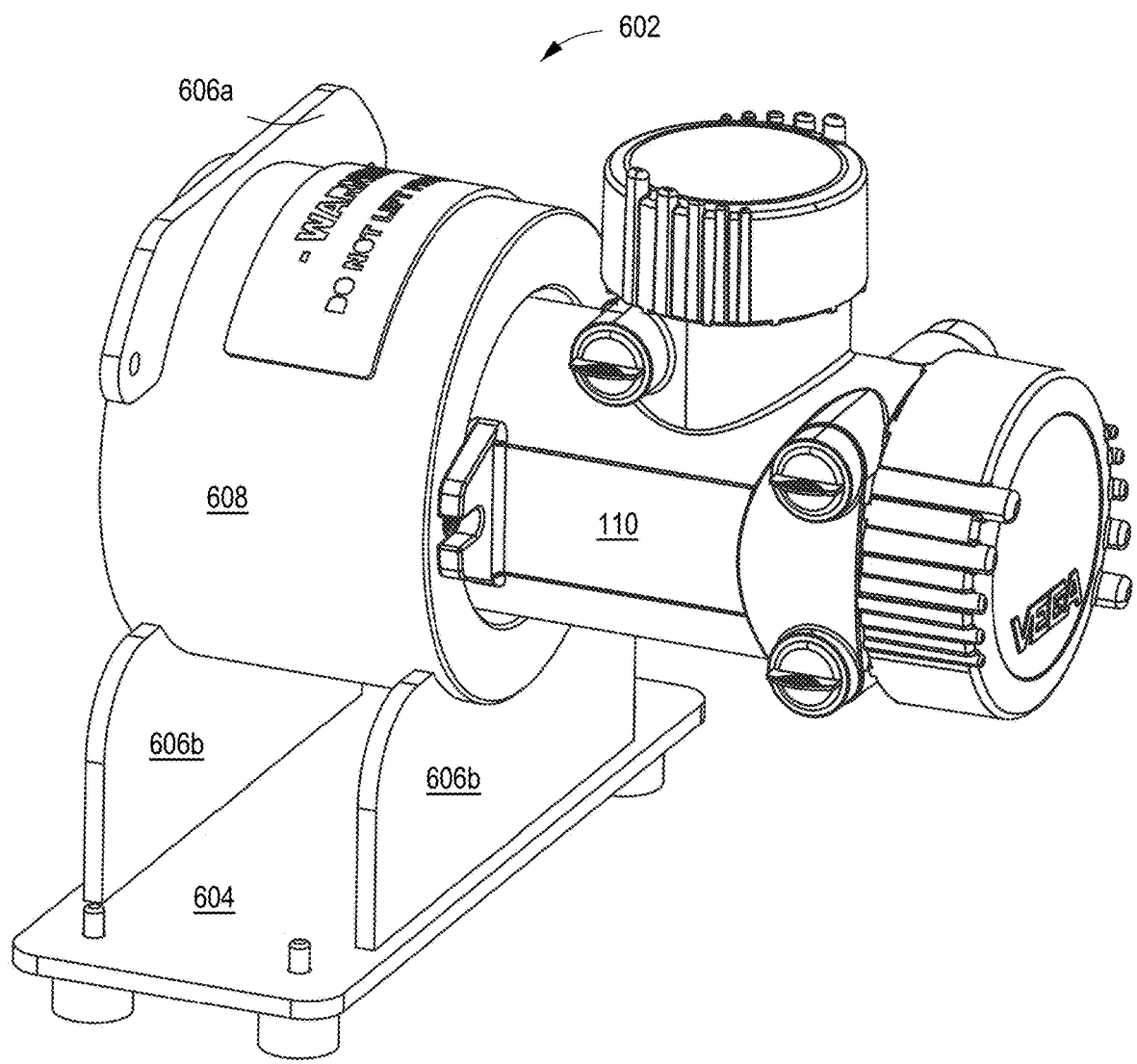
FIG. 6B illustrates a perspective view of a nuclear detector and a detector bracket assembled.

FIG. 6A illustrates an exploded view of a nuclear detector 110 and a detector bracket 602. FIG. 6B illustrates a perspective view of a nuclear detector 110 and a detector bracket 602 assembled.

Referring to FIGS. 6A-B, the detector bracket 602 may include a base plate 604, mounting plates 606a-c, and a cylinder 608. The base plate 604, the mounting plates 606a-c, and the cylinder 608 may be coupled, e.g., via welding. The base plate 604 may be coupled to an upper surface of an upper plate 104 (see FIGS. 4A-C). vibration dampeners 116 may be disposed between the base plate 604 and the upper plate 104 (see FIG. 4A-C).

Additionally, the nuclear detector 110 may be coupled to the cylinder 608. A portion of the nuclear detector 110 may extend through the cylinder 608.

When coupled to the upper plate 104, the nuclear detector 110 may be aligned with a nuclear source 108 (see FIGS. 4A-B). In other words, nuclear particles or radiation emitted from the nuclear source 108 would travel on a path in the direction of the nuclear detector 110. The emitted nuclear particles or radiation would be detectable by the nuclear detector 110.

Figure 7:
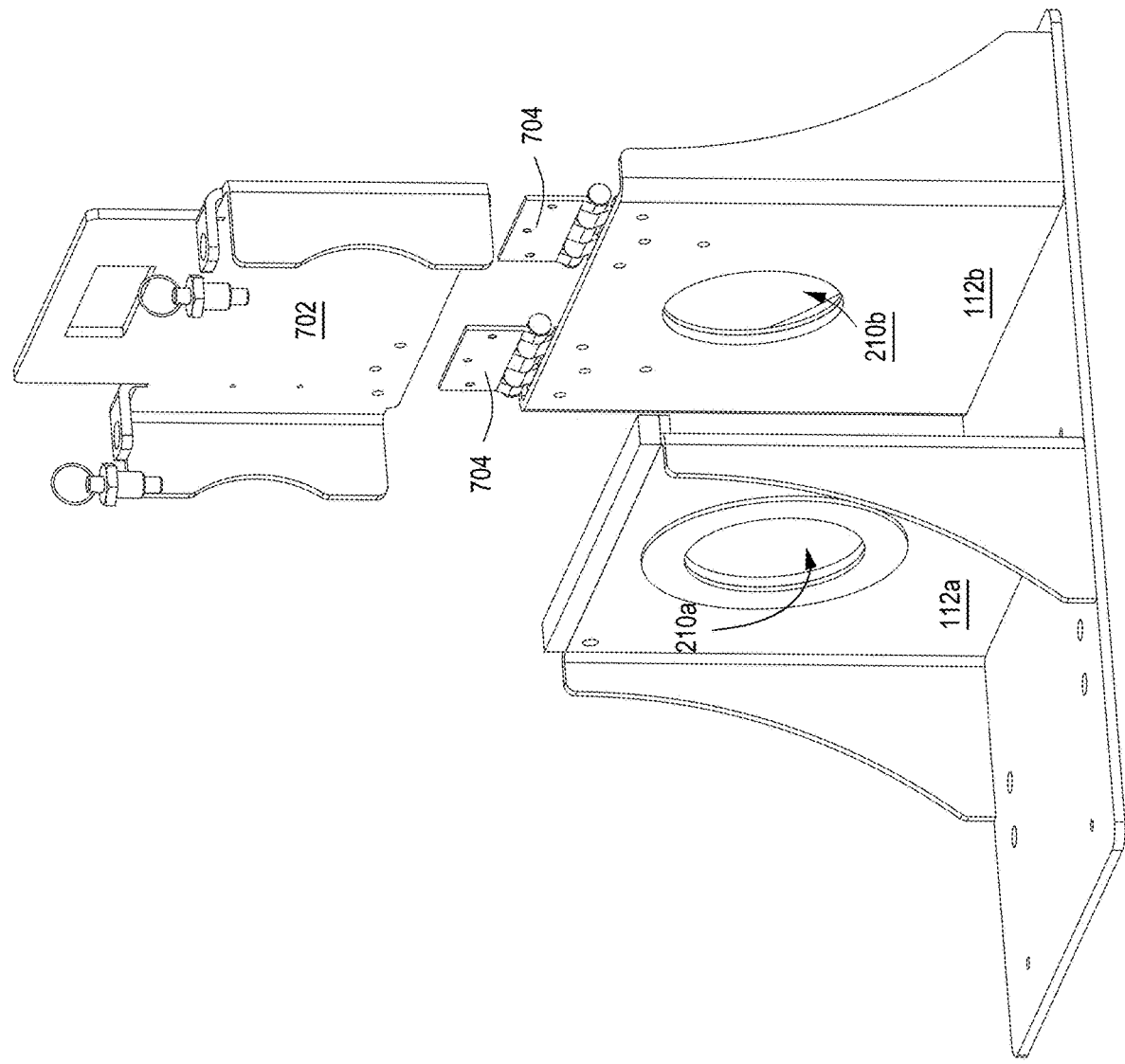
FIG. 7 illustrates shields coupled to an upper plate.

FIG. 7 illustrates shields 112a, 112b coupled to an upper plate 104. The shields 112a, 112b may be coupled to an upper surface of the upper plate 104. Each shield 112 may be a flat plate having end-portions bent at approximately 90 degrees, forming three contiguous walls. The three walls may form a block-letter C. Additionally, each shield may have an aperture 704 extending through a middle wall of the three walls. The shields 112a, 112b may be aligned so that apertures 210a, 210b may be aligned.

Also, a cover 702 may be coupled to the shield 112b. Hinges 704 may be coupled to and edge of the cover 702 and an upper edge of the shield 112b. Accordingly, the cover 702 may be pivotably coupled to the shield 112b.

Figure 8A:
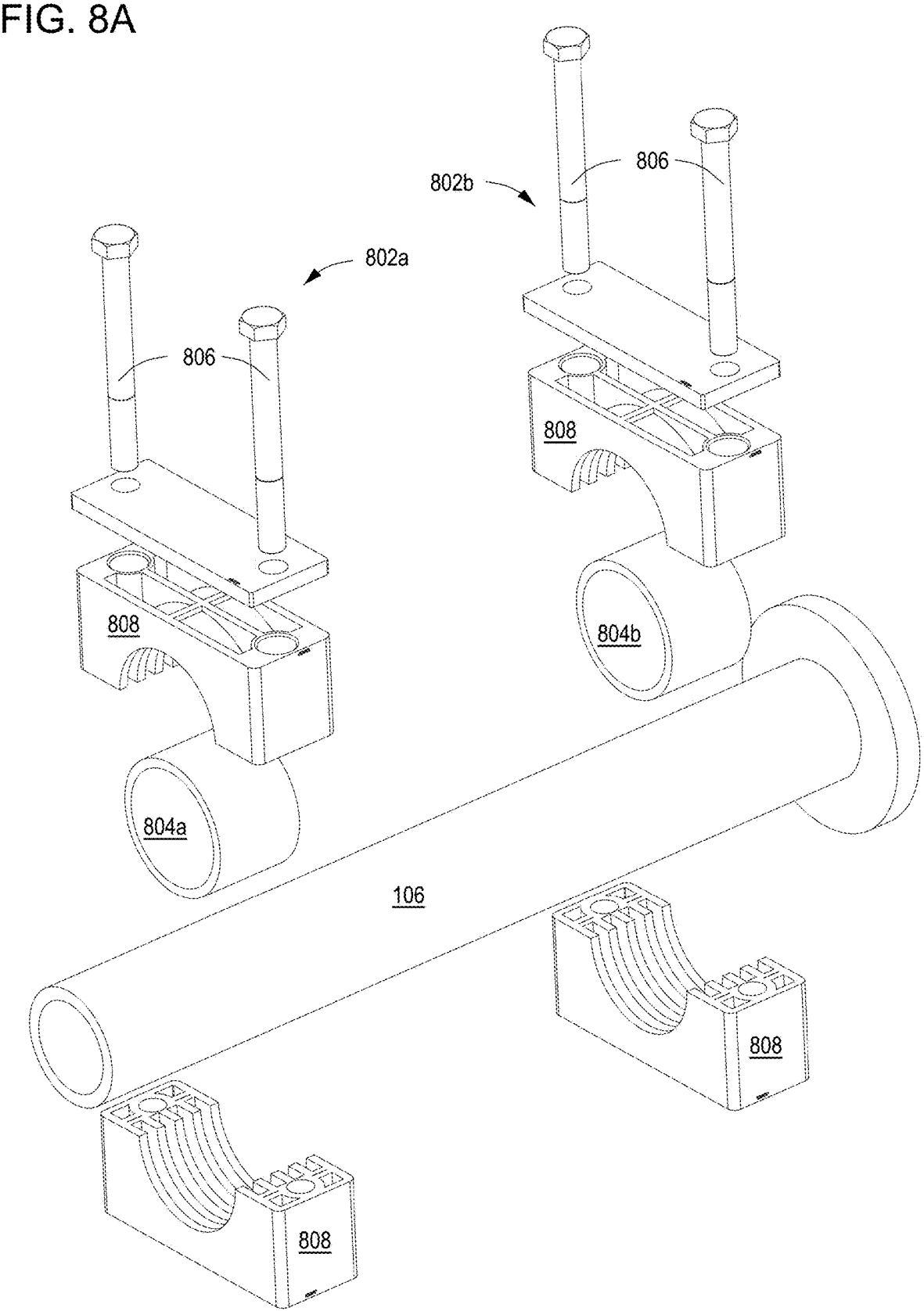
FIG. 8A illustrates an exploded view of a pipe, clamps, and vibration dampeners.
Figure 8B:
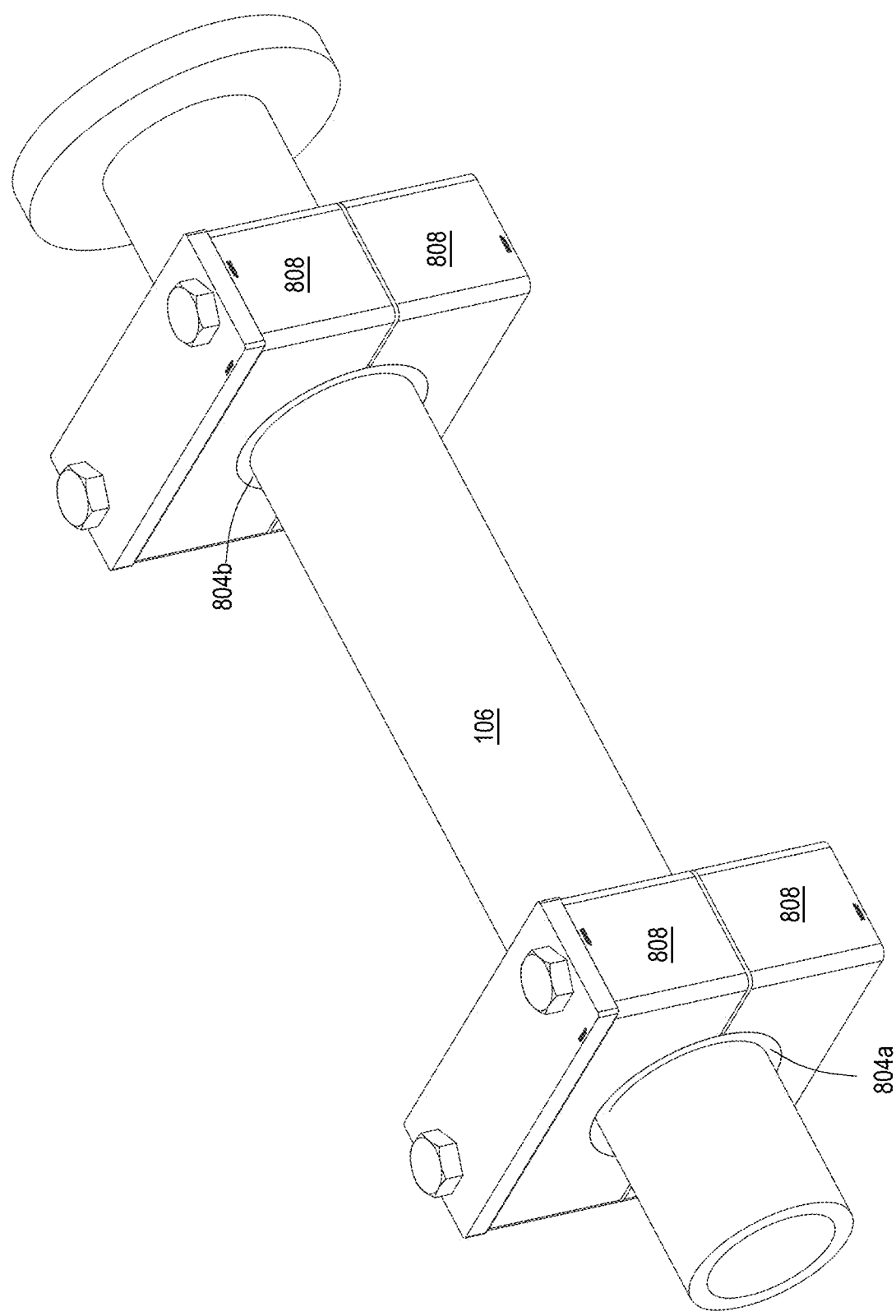
FIG. 8B illustrates a perspective view of a pipe, clamps, and vibration dampeners assembled.

FIG. 8A illustrates an exploded view of a pipe 106, clamps 802a, 802b, and vibration dampeners 804a, 804b. FIG. 8B illustrates a perspective view of a pipe 106, clamps 802a, 802b, and vibration dampeners 804a, 804b assembled.

Referring to FIGS. 8A-B, vibration dampeners 804a, 804b may be coupled to a pipe 106. The vibration dampeners 804a, 804b may be cylindrical. Additionally, the vibration dampeners 804a, 804b may have inner diameters larger than an outer diameter of the pipe 106. Accordingly, portions of the pipe 106 may be extended through the vibration dampeners 804a, 804b.

Clamps 802a, 802b may be coupled around the vibration dampeners 804a-b. Each clamp 802 may have two C-shaped portions 808. The two C-shaped portions 808 may be coupled together to form an aperture extending therethrough. The coupled C-shaped portions 808 may form a block-letter "0." A portion of the pipe 106 and a vibration dampener 804 may be disposed in the aperture.

Bolts 806 may extend through the C-shaped portions 808 of each clamp 802. Furthermore, the bolts 806 may have ends coupled to support posts 118 (see FIGS. 1 and 4A). Thus, the bolts 806 may retain the clamps 804a, 802b against the support post 118a, 118b (see FIGS. 4B-C).

During fracturing of oil and/or gas wells, various operations may require quick, accurate density measurements of fluid flowing through a frac pipe extending downhole. Nuclear densitometer assemblies 100 as those described above may be used to take such measurements.

However, before using a nuclear densitometer assembly 100 at a well location, the nuclear densitometer assembly 100 may be transported to the location. The nuclear densitometer assembly 100 may be transported on a bed of a vehicle over rough, bumpy terrain. During transit, the vehicle may shake, sway, and/or bounce, which may cause the bed of the vehicle to impart impact against a lower plate 102 of the nuclear densitometer assembly 100. Vibration dampeners 116 disposed on the lower plate 102 may absorb force from the impact and/or vibration generated by the impact to the lower plate 102. Accordingly, a nuclear source 108 and a nuclear detector 110 coupled to an upper plate 104 of the nuclear densitometer assembly 100, in some cases, may receive little or no vibration and/or force from the impact.

Referring to FIGS. 2, 3, and 4A-B, a worker may couple a nuclear densitometer assembly 100 to a portion of a pipe 106. If the nuclear densitometer assembly 100 is required to be lifted or repositioned, the feet 120 and/or the lift brackets 122 could be used. Cables from a hoist or a crane may be coupled to the lift brackets 122. An operator may cause the hoist or the crane to lift the nuclear densitometer assembly 100. Alternatively, the operator may operate a forklift and extend tines of the forklift through the feet 120a, 120b. The operator may operate the forklift to move the nuclear densitometer assembly 100.

Having positioned the nuclear densitometer assembly 100 relative to the pipe 106, the worker may position the pipe 106 on support posts 118a, 118b. Next, the worker may position a support pad 202 between the pipe and each support post 118. Also, the worker may position a portion of the pipe 106 between shields 112a, 112b. The pipe 106 and the shields 112a, 112b may be arranged such that the pipe 106, in some cases, does not physically touch either of the shields 112a, 112b, e.g., so that there is a gap between each shield 112 and the pipe 106. Accordingly, the pipe 106 may be positioned between a nuclear source 108 and a nuclear detector 110. Moreover, the pipe 106 may be disposed between collimators 114a, 114b (see FIGS. 2 and 3).

Referring to FIGS. 4B-C and 7B, the operator may pivot a cover 702 to a closed position, e.g., perpendicular to the shields 112a, 112b. In the closed position, the cover 702 may be disposed above the pipe 106. The cover 702 may have an aperture having a latch 502 extending therethrough. The operator may couple a lock (not shown) to the latch 502. In some cases, the lock may inhibit the cover 702 from being pivoted away from the latch 502. Therefore, in some cases in the closed position, the cover 702 may retain the pipe 106 between the shields 112a, 112b, the nuclear source 108, and the nuclear detector 110.

During completion or fracturing operations, the worker may send a large volume of fluid through the pipe 106. The fluid may include fracturing chemicals, proppants, pounds proppant additive, water, cement, lubricant, cleaning chemicals, slurry, coated sand, sand, and oil. Next, the worker may cause the nuclear source 108 to emit nuclear particles or radiation. The emitted nuclear particles or radiation may travel from the nuclear source 108 to the nuclear detector 110.

The emitted nuclear particles or radiation may travel through the inner bore of the first collimator 114a, the aperture 210a of the shield 112a, the pipe 106, the aperture 210b of the shield 112b, and the inner bore of the second collimator 114b to the nuclear detector 110 (see FIGS. 2 and 3).

In some versions, the emitted nuclear particles or radiation may travel through an aperture 210a of the shield 112a, the pipe 106, and the aperture 210b of the shield 112b to the nuclear detector 110 (see FIGS. 4A-C).

Accordingly, the emitted particles or radiation may travel on a path intersecting the flowing fluid in the pipe 106. Some of the emitted particles may be blocked or absorbed by the flowing fluid while some of the emitted particles may pass through the flowing fluid. The nuclear detector 110 may receive a portion of those emitted nuclear particles or radiation that do pass through the flowing fluid. The nuclear detector 110 may register the number of particles or amount of radiation it receives. Afterwards, the number of received nuclear particles or amount of radiation may then be used to calculate density of the flowing fluid.

Often, the fluid may flow at high velocity in the pipe 106. Accordingly, the flow of the fluid in the pipe 106 may cause turbulence within the pipe 106. The turbulence in the pipe 106 may cause the pipe 106 to vibrate (sometimes violently). Vibrations from the pipe 106 may be problematic if they reach the nuclear source 108 and/or the nuclear detector 110. Over time, the nuclear source 108 and/or the nuclear detector 110 may become damaged after receiving such vibrations. However, the nuclear densitometer assembly 100 may mitigate damaging vibrations from reaching the nuclear source 108 and/or the nuclear detector 110.

Because the pipe 106 is coupled, e.g., clamped, to the lower plate 102, vibration from the pipe 106 may be transferred to the lower plate 102. However, some of the vibration may be absorbed or diminished by the support pads 202 disposed between the pipe 106 and the support 118a, 118b extending from the lower plate 102. Additionally, vibration dampeners 116 disposed on the lower plate 102 may further absorb vibration from the pipe 106. Accordingly, in some cases, little or no vibration may be transferred to the upper plate 104. Moreover, the nuclear source 108 and the nuclear detector 110 coupled to the upper plate 104, in some cases, may receive little to no vibration from the pipe 106.

What is claimed as the invention is:

1. A nuclear densitometer assembly for measuring a density of a fracturing fluid in a pipe, comprising:
    a lower plate;
    a support post extending from the lower plate, the support post capable of supporting a portion of the pipe;
    an upper plate;
    a nuclear source coupled to the upper plate;
    a nuclear detector coupled to the upper plate;
    wherein a portion of the pipe is capable of being disposed between the nuclear source and the nuclear detector.

2. The nuclear densitometer assembly of claim 1, wherein the lower plate comprises one or more feet.

3. The nuclear densitometer assembly of claim 1, wherein the lower plate comprises one or more feet extending from a lower surface of the lower plate.

4. The nuclear densitometer assembly of claim 1, wherein the lower plate comprises one or more lift brackets.

5. The nuclear densitometer assembly of claim 1, wherein the lower plate comprises one or more lift brackets extending from an upper surface of the lower plate.

6. The nuclear densitometer assembly of claim 1, further comprising a clamp capable of being coupled to the support post.

7. The nuclear densitometer assembly of claim 1, further comprising a clamp capable of being coupled to a portion of the pipe.

8. The nuclear densitometer assembly of claim 1, further comprising a support pad capable of being disposed between a portion of the pipe and the support post.

9. The nuclear densitometer assembly of claim 1, further comprising a support pad capable of being abutted against a portion of the pipe and the support post.

10. The nuclear densitometer assembly of claim 1, further comprising a support pad comprising an elastomer.

11. The nuclear densitometer assembly of claim 1, wherein a central axis of the pipe is oblique to a nuclear beam capable of being generated by the nuclear source.

12. The nuclear densitometer assembly of claim 1, wherein a central axis of the pipe is capable of being oblique to an open path between the nuclear source and the nuclear detector.

13. The nuclear densitometer assembly of claim 1, wherein the nuclear detector is capable of detecting particles or radiation emitted by the nuclear source.

14. The nuclear densitometer assembly of claim 1, further comprising:
    a first collimator;
    a second collimator, wherein the first collimator shares a central axis with the second collimator;
    a first shield having an aperture aligned with an opening of the first collimator; and
    a second shield having an aperture aligned with an opening of the second collimator;
    wherein the aperture of the first shield and the aperture of the second shield are aligned.

15. The nuclear densitometer assembly of claim 1, further comprising:
    a collimator having a central axis; and
    a shield having a plane oblique to the central axis.

16. The nuclear densitometer assembly of claim 1, further comprising:
    a first collimator;
    a second collimator, wherein the first collimator shares a central axis with the second collimator;
    a first shield having an aperture aligned with an end of the first collimator; and
    a second shield having an aperture aligned with an end of the second collimator, wherein the aperture of the first shield and the aperture of the second shield are aligned.

17. The nuclear densitometer assembly of claim 1, further comprising:
    a first collimator;
    a second collimator, wherein the first collimator shares a central axis with the second collimator; and
    a shield disposed between the first collimator and the second collimator, wherein the shield has a plane oblique to the central axis.

18. A nuclear densitometer assembly for measuring a density of a fracturing fluid in a pipe, comprising:
    a lower plate;
    a support post extending from the lower plate, the support post capable of supporting a portion of the pipe;
    an upper plate;
    a vibration dampener disposed between the lower plate and the upper plate;
    a nuclear source coupled to the upper plate;
    a nuclear detector coupled to the upper plate;
    wherein a portion of the pipe is capable of being disposed between the nuclear source and the nuclear detector.

19. The nuclear densitometer assembly of claim 18, wherein the vibration dampener comprises an elastomer.

* * * * *